United States Patent [19]
Harris

[11] Patent Number: 5,798,531
[45] Date of Patent: Aug. 25, 1998

[54] SYSTEM FOR DETECTING SMALL HOLES IN MOVING ARTICLES

[75] Inventor: David E. Harris, Powell, Ohio

[73] Assignee: Harris Instrument Corporation, Delaware, Ohio

[21] Appl. No.: 661,214

[22] Filed: Jun. 10, 1996

[51] Int. Cl.[6] .................. G01B 11/04; G01N 21/00
[52] U.S. Cl. .................. 250/559.03; 250/559.45; 250/559.46; 356/430; 356/431
[58] Field of Search .................. 250/208.1, 208.2, 250/559.03, 559.45, 559.46, 559.48, 214 A; 356/237, 238, 430, 431

[56] References Cited

U.S. PATENT DOCUMENTS

| | | | |
|---|---|---|---|
| 3,588,513 | 6/1971 | Takasuki et al. | 356/430 |
| 3,589,816 | 6/1971 | Sugaya | 356/430 |
| 3,655,989 | 4/1972 | Robinson | 356/431 |
| 3,697,758 | 10/1972 | Binks | 250/202 |
| 3,835,332 | 9/1974 | Bridges | 356/430 |
| 3,859,538 | 1/1975 | Mannonen | 356/430 |
| 4,559,451 | 12/1985 | Curl | 356/431 |
| 4,711,579 | 12/1987 | Wilkinson | 356/375 |
| 5,546,808 | 8/1996 | Harris | 73/618 |

*Primary Examiner*—Stephone B. Allen
*Attorney, Agent, or Firm*—Standley & Gilcrest

[57] ABSTRACT

A small hole detection system which detects small holes in fast moving sheets of material. An array of LEDs is pulsed from an emitter which is aligned with an array of photocells positioned to detect light emitting from the emitter. The receiver sends a signal to a processing unit when light is detected. The small hole detection system may include an auto-shuttering mechanism which automatically adjusts the system according to the width of the material being scanned.

20 Claims, 13 Drawing Sheets

TO FIG. 10B

SYSTEM FOR DETECTING SMALL HOLES IN MOVING ARTICLES

BACKGROUND AND SUMMARY OF THE INVENTION

The present invention relates generally to a system and method for detecting small hole defects in materials.

Recently, material suppliers have been under increasing pressure for built-in quality and zero defect production programs for the materials they supply. Traditionally, small holes or defects in strips of material, such as sheet metal, have been difficult to find. Although pin hole inspection systems have existed for some time, these traditional systems are designed to detect holes in the micron range and are vital to the production and inspection of materials used in the manufacturing of products such as food containers and medical supplies. Unfortunately, these systems are expensive and difficult to operate in many industrial environments. Line scan camera surface inspection systems are currently being developed to detect various types of defects, including small holes. Like the earlier pin hole detector systems, they are expensive and difficult to install effectively in many industrial situations. Such known systems have often proved unreliable. One small hole in an otherwise perfect material can cost thousands of dollars in lost production.

The small hole detection system of the present invention is designed to overcome many of the problems associated with small hole defect inspection technology. The present invention is cost effective, easy to install, substantially maintenance free, and capable of detecting small holes in fast moving strips of material. The present invention delivers highly reliable service in the industrial environments where it is needed most.

Traditional hole detect systems had to be manually or mechanically adjusted to the width of the strip being scanned. This slowed the scanning process and required additional human intervention. The present invention contains a unique auto adjustment feature which allows the system to automatically adjust to the width of the strip being scanned.

Additionally, traditional hole detect systems utilized photomultiplier devices which were very expensive and unreliable. The present invention detects small holes without the use of photomultiplier devices thus reducing cost and increasing reliability.

Traditional hole detect systems have used high power lamps which require high energy considerations. The present invention utilizes LEDs which are used to scan the material strips. These LEDs are arranged and pulsed in a unique arrangement. Since the LEDs may not tolerate continued application of the high energy needed for small hole detection, the LEDs of the present invention are pulsed at a predetermined frequency to preserve the life of the LEDs. Pulsing at a predetermined frequency also makes stray light from the ambient environment a non-factor in the operation of the invention.

In summary, the present invention has many advantages over traditional hole detection systems, including:

1) detects holes or defects as small as 0.05" (inches) (1.27 mm);
2) operational on lines with speeds as high as 3000' (feet) per minute;
3) solid state reliability;
4) no moving parts, therefore, less likely to wear out;
5) dust, mist, and vibration tolerant;
6) easy to install, simple to maintain;
7) no light sources to replace;
8) low voltage system with no high voltage necessary;
9) auto-shuttering feature;
10) not sensitive to ambient light; and
11) relatively inexpensive.

These and other objects of the invention, as will be apparent herein, are accomplished by the hole detection system of the present invention which in one preferred embodiment comprises:

an array of LEDs; an array of photocells positioned directly across from the array of LEDs for detecting light emitted from the array of LEDs; a preamplifier circuit electrically connected to the photocells; a video processing circuit, electrically connected to the preamplifier circuit for processing a video signal from the preamplifier circuit and where the video processing circuit outputs an appropriate video signal when a hole is detected in the moving sheet product; a processing unit electrically connected to the video processing circuit for processing a video signal from the video processing circuit, and where the processing unit indicates when a hole in the moving sheet material has been detected.

It is preferred that the video processing circuit be comprised of: a sharply tuned bandpass filter electrically connected to the preamplifier circuit for filtering the video signal from the preamplifier circuit; a sample and hold amplifier electrically connected to the output of the preamplifier circuit; a comparator, electrically connected to the output of the sample and hold amplifier for filtering noise; and where the comparator switches to a higher voltage when the video signal from the preamplifier circuit exceeds the threshold voltage of the comparator.

It is also preferred that the processing unit be comprised of: a hole detect circuit electrically connected to the video processing circuit for triggering a hole detect signal when a hole is detected on the moving sheet material; and a "Fail-Safe" circuit electrically connected to the hole detect circuit for insuring that the hole detection system is scanning properly.

It is preferred that the processing unit be further comprised of: an edge counting circuit electrically connected to the hole detect circuit for counting edges detected in a scan; and a cylindrical lens which allows for closer spacing of the array of LEDs to the array of photocells to accommodate limited space requirements and to improve the signal to noise ratio of the hole detection system.

It is also preferred that the array of LEDs be comprised of: a first section of 50 LEDs; a second section of 50 LEDS; where these first and second sections of 50 LEDs be comprised of five groups of 10 LEDS; and where the first and second sections of LEDs are pulsed at a 20 kHz repetition rate.

BRIEF DESCRIPTION OF THE DRAWINGS

Novel features and advantages of the present invention in addition to those mentioned above will become apparent to those skilled in the art from a reading of the following detailed description in conjunction with the accompanying drawings, in which.

DETAILED DESCRIPTION OF THE PREFERRED EMBODIMENTS

The preferred system herein described is not intended to be exhaustive or to limit the invention to the precise forms disclosed. The preferred embodiment is described to explain the principles of the invention, and the application of the method to practical uses, so that others skilled in the art may practice the invention.

Figure 1:
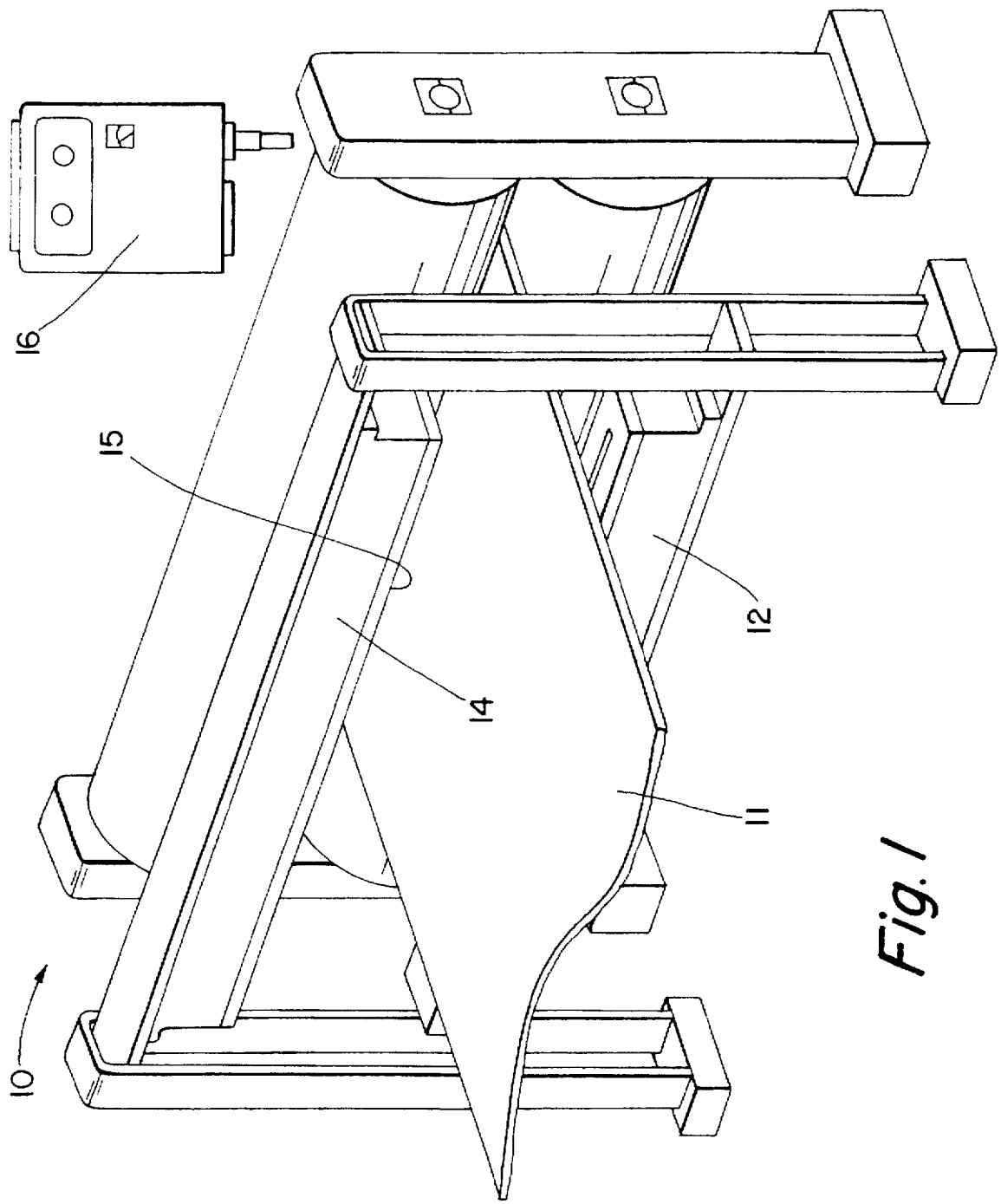
FIG. 1 illustrates a preferred embodiment of a Small Hole Detection System of the present invention.

Referring in more detail to the drawings and particularly FIG. 1, a Small Hole Detection System 10 is shown. The Small Hole Detection System is comprised of an emitter 12, a receiver 14, and a processing unit 16. The emitter 12 and receiver 14 have preferred scan ranges from 10 inches to 40 inches in length (an emitter 12 with a 10 inch scan range will hereinafter be referred to as a 10 inch emitter). Multiple emitters 12 and receivers 14 can be used to cover strips with greater widths. Although the technology is the same for all sizes, the following detailed description will focus on the specific dimensions of the 10 inch long emitter 12 and receiver 14.

Figure 2:
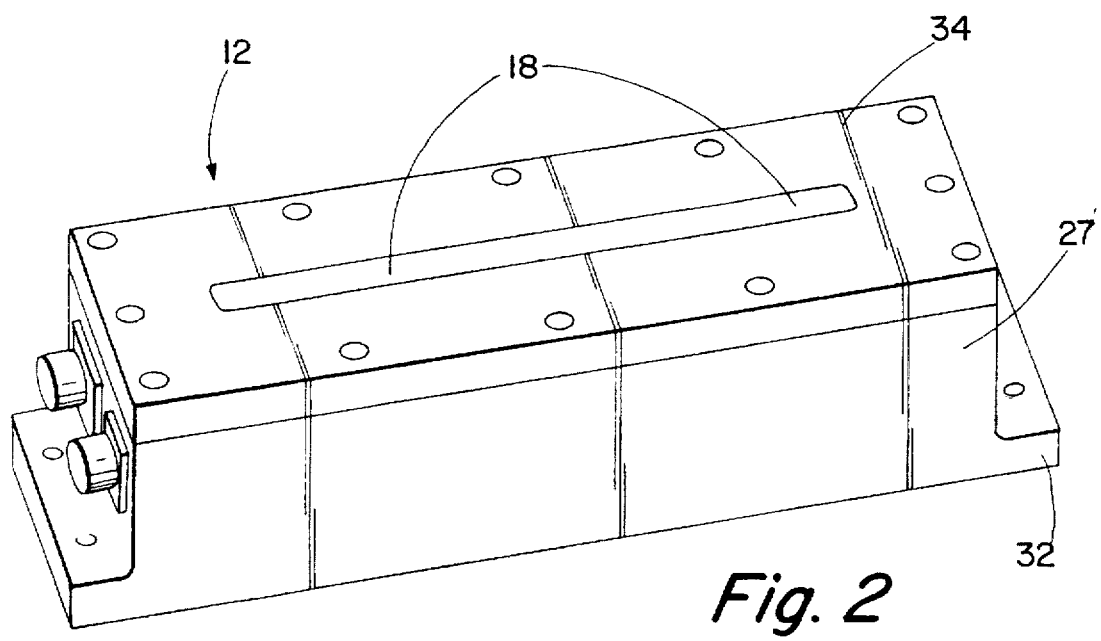
FIG. 2 illustrates a perspective view of one embodiment of an emitter of the Small Hole Detection System of the present invention.
Figure 13:
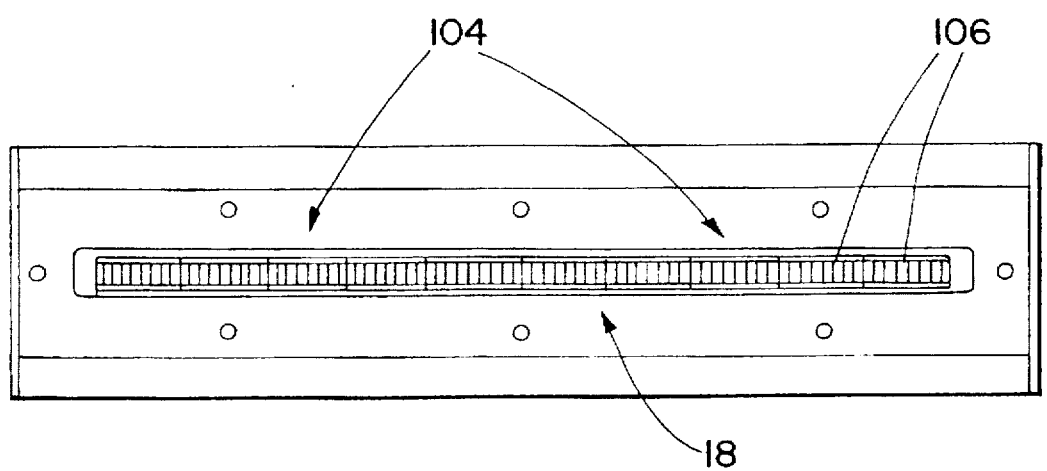
FIG. 13 illustrates a plan view of the LED array.

FIG. 2 illustrates a perspective view of an emitter 12 (a 10 inch long emitter module). The emitter 12 integrates a mounting plate 32 into the base of the emitter 12. The emitter 12 is preferably constructed of an extruded aluminum tube for the housing 27 with an extruded aluminum mounting plate 32 and an extruded aluminum bezel 34 with a borosilicate glass lens as the emitter window. The emitter 12 and receiver 14 are preferably housed in similar housings. The emitter 12 preferably contains 100 high intensity light emitting diodes (LEDS), or diodes, which are evenly distributed in a linear array shown at 18. (The array of LEDs may be replaced with any type of electromagnetic radiation emitting devices.) The diodes emit light out of the top of the emitter window. There is generally a 0.1 inch [2.54 mm] spacing between each LED. FIG. 13 illustrates one embodiment of the LED array 18. The LED array 18 is divided into two sections 104 of 50 diodes each. Each section is further divided into 1 inch [2.54 cm] long groups 106 of ten LEDS. The 50-diode sections 104 are pulsed (or energized) alternately at a 20 kHz repetition rate to permit 100 usec high-speed hole detection. As additional 10 inch modules are added to the emitter 12, they operate in parallel with the first module. Therefore, the entire emitter 12 is scanned in the same 100 usec time as the first module, regardless of emitter 12 length.

The "distributed cell" receiver 14 may also be constructed with 10 inch modules. Each receiver 14 contains an array 15 of 10 separate infrared sensitive silicon cells (or photocells). The silicon cells 20 are evenly distributed along the length of the receiver at 15. The silicon cells 20 are placed opposite the array of LEDS 18 of the emitter 12. A 10 inch long cylindrical lens concentrates the field of view for each ten-cell detector array 15. The 10 inch long cylindrical lens is placed over the entire array 15 of silicon cells 20 generally at 22.

Figure 3:
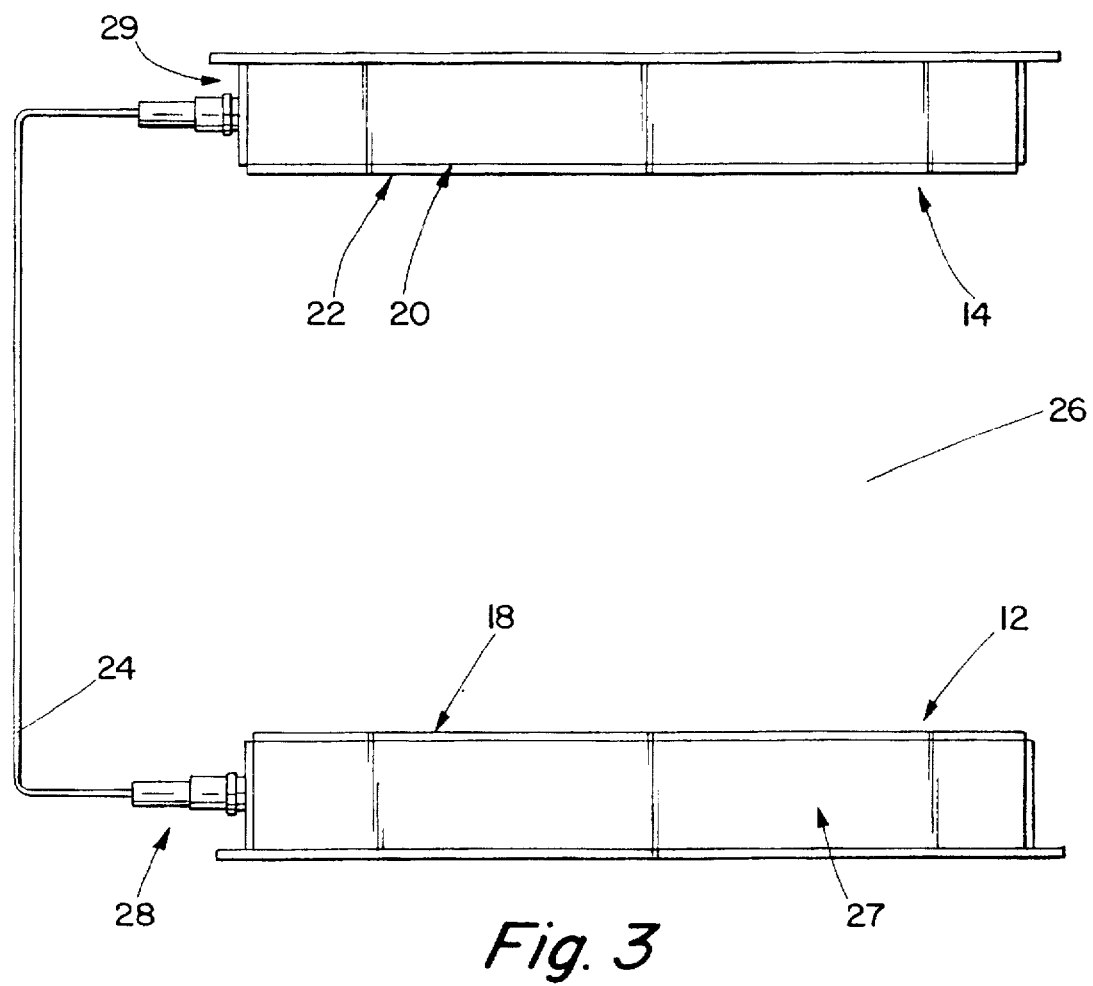
FIG. 3 illustrates a sensor of the Small Hole Detection System of the present invention.

The emitter 12 and the receiver 14 are connected by a receiver-to-emitter cable 24 to form a sensor 26 as shown in FIG. 3. Each receiver 14 contains a low-noise video amplifier 42 (or "preamplifier") with a tuned 20 Khz band-pass filter. The outputs from up to four separate preamplifiers 42 is preferably added together in the receiver summing amplifier 50 and delivered to the video processing circuits 60 in the emitter 12 via the receiver-to-emitter cable 24.

The emitter housing 27 contains video processing circuitry 60 for the video signal from the receiver 14. The video output signal from the emitter 12 is a CMOS logic signal whenever a hole is detected in the strip 11 of material being scanned. The emitter 12 also supplies a SYNC pulse at the beginning of each new scan.

Alternatively, the emitter 12 and receiver 14 may be assembled for operation in extreme operating conditions (such as high collision environments). In this "ultra-tough" environment, the emitter 12 is constructed of cast aluminum housings (approximately 0.624 inches thick) with an extruded aluminum bezel (approximately 0.75 inch thick) with a borosilicate glass emitter window (approximately 0.375 inches thick).

The one-inch long LED groups 106 may be pulsed in groups of 5 at a 20 kHz rate to insure high speed detection of rapidly moving holes. The modular design of the emitter 12 and receiver 14 circuit boards permits the construction of sensors 26 in ten-inch increments from 10 inches to 40 inches in scan length.

Special infrared filtered silicon photocells 20 are used in the receivers 14. These photocells 20 reject 95 percent of the visible light spectrum and respond specifically to the emitter light source. The optical arrangement of the photocells 20 permits multiple path detection for each LED in the emitter array 18. The side spacing of the photocells 20 permits light to be sensed even where thicker material might limit the view angle of the photocells 20. The use of a long receiver lens at 22 allows for closer spacing of the emitters 12 and receivers 14 to accommodate limited space requirements and improve the system's signal to noise ratios.

Figure 4:
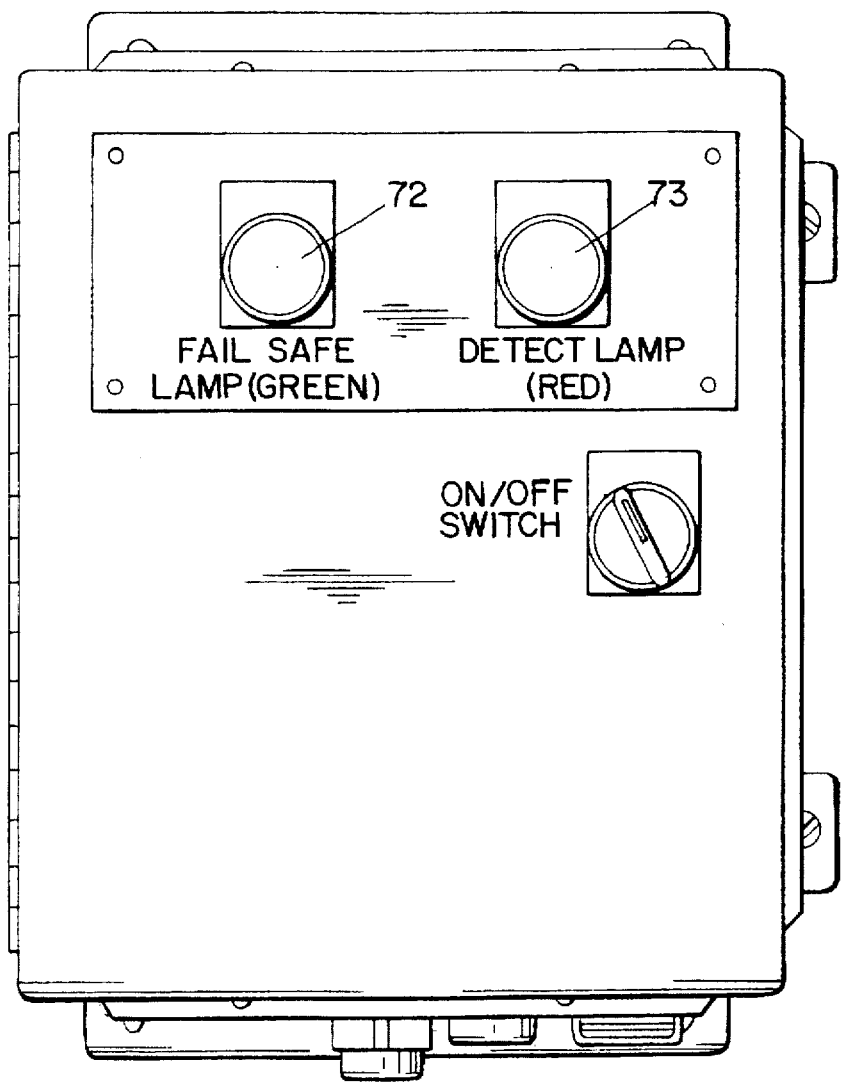
FIG. 4 illustrates one embodiment of the processing unit of the present invention.
Figure 5:
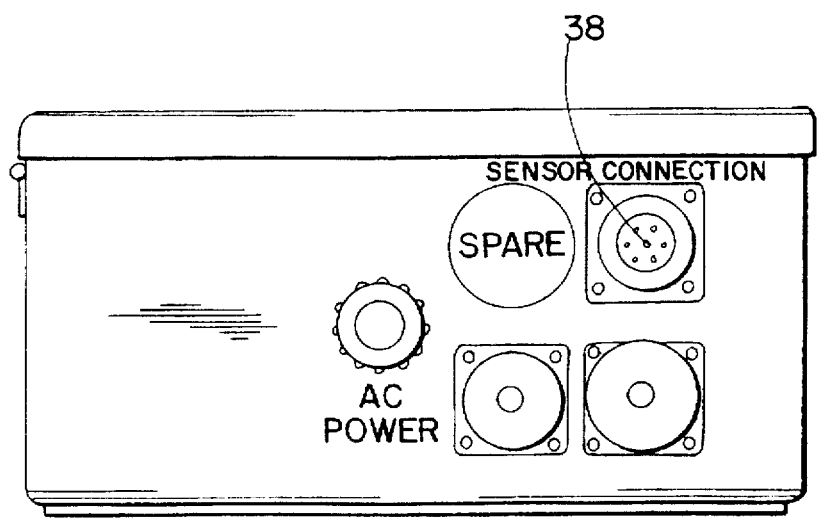
FIG. 5 illustrates the bottom view of the processing unit of FIG. 4.

The sensors 26 are connected to the processing unit 16. The processing unit 16 also supplies relay contacts and indicator lamps for fail-safe monitoring and hole detect signal processing. The display and relay closure time for a hole detect event is adjustable from 0.05 seconds to 10.00 seconds. In the preferred embodiment the processing unit 16 has a standard 120 volt, 50–60 Hz, or an optional 220 volt, 50–60 Hz, power supply. FIG. 4 illustrates one embodiment of the processing unit 16. FIG. 5 shows the bottom of the processing unit 16 of FIG. 4. The emitter cable from the emitter 12 connects to the input at 38. The processing unit 16 is designed to provide signal processing, operator interface with the hole detection system 10, and a regulated power source for a single sensor 26.

The emitter 12 and receiver 14 are mounted in parallel, with the receiver 14 directly above the emitter 12. Again, the LED array 18 is positioned to emit light toward the array 15 of silicon photocells 20. The centerline of the emitter 12 and receiver 14 should be perpendicular to the strip 11, with a maximum tip of (+or−) 2 degrees. A greater emitter-to-receiver spacing creates a greater requirement for proper aim adjustment.

Although ambient light sources are largely rejected by the 20 kHz tuning of the video signal processing circuits 60 and the IR filtering in the silicon cells 20, some interference may be experienced. Strobe lights and pulsed IR light sources can pose special problems for the sensor 26. Keeping the field of view of the sensor 26 as small as possible with close emitter-to-receiver spacing will reduce the possibility of false hole detections while also improving small hole sensitivity. Shielding the receiver 14 from interfering light sources to reduce such ambient light interference will improve performance.

The maximum detection width range for the sensor 26 varies depending upon the length of the emitter 12. However, operational characteristics, such as side-to-side strip 11 deviation and product passline (defined as distance from the emitter face to the strip 11 bottom face) can lessen that range. The sensor 26 should be placed on the line where strip 11 side-to-side position is relatively stable to prevent loss of range from side-to-side deviation. Typically the detection width range is approximately 1 inch less than the length designation of the sensor 26 (e.g. a 10 inch sensor 26 will have an effective detection width range of 9 inches.).

Figure 6:
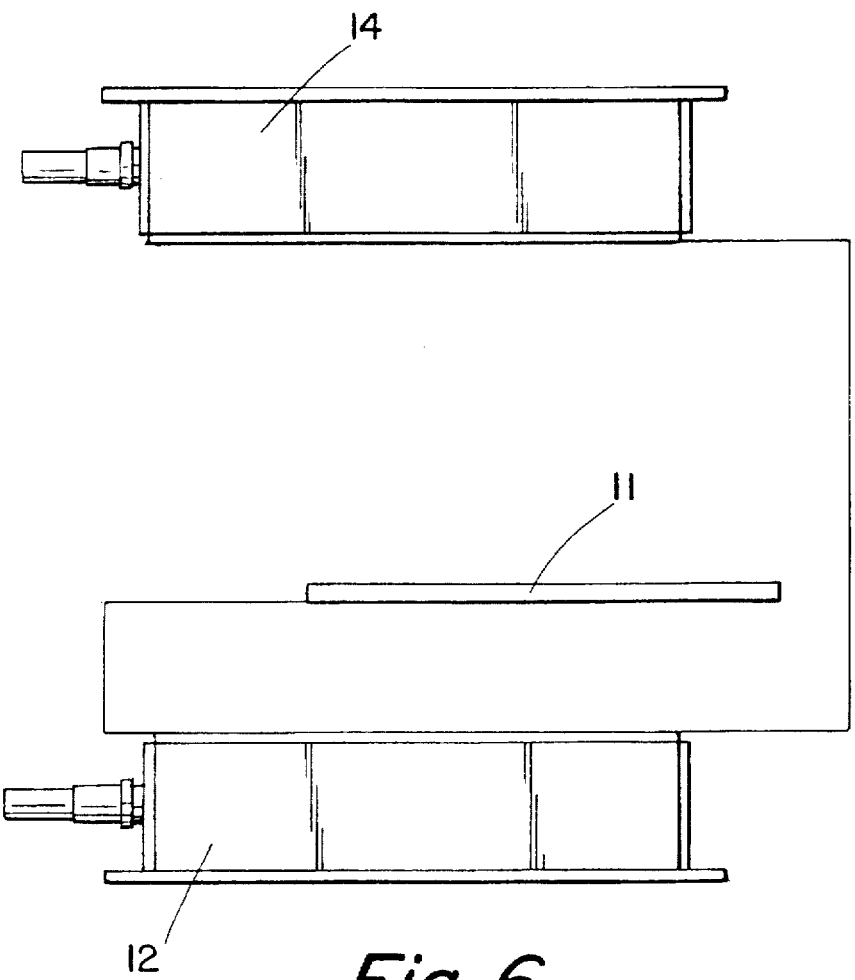
FIG. 6 illustrates the preferred emitter-to-receiver and product passline spacing.

Preferred product passline spacing for the sensor 26 is from 2 inches to 4 inches, with a preferred spacing of 2 inches (see FIG. 6). Spacing the product passline closer than 2 inches will decrease the time the sensor 26 has to scan for a hole. As the product passline increases, the active inspection range of the sensor 26 decreases, so a passline spacing higher than 4 inches may degrade the detection abilities of the system 10 allowing small holes to move away from the emitter 12 before being detected by the sensor 26.

Although the LEDs are preferably pulsed in sections 104 of 50, each one-inch, 10 LED, group 106 may be activated or deactivated to scan a specific material 11 width. This permits the small hole detection system sensor 26 to be automatically adjusted for different strip widths. This automatic adjustment, or "auto-shuttering", is initiated each time power is interrupted and reapplied to the sensor 26. The Auto-shutter setup sequence starts by lighting all the LEDs in the emitter array 18 (with the strip 11 in position). If the light is detected in the receiver 14 at this time, the first one-inch group 106 of the LED array 18 is deactivated. The LEDs are then lighted, with the first group 104 deactivated. As the sequence progresses, each time light is detected by the receiver 14, an additional one-inch group 106 of the array 18 is extinguished, until no light is detected by the receiver 14. When no more emitter 12 LEDs can be detected, the strip 11 is effectively covering any lighted LEDs in the emitter 12. (If this shuttering process is not initiated, the sensor 26 will indicate a hole has been detected when scanning a strip 11 that is narrower than the sensor array 18—since the LEDs that are not covered by the strip 11 will activate the silicon cell 20 detectors in the receiver 14). As the auto-shutter sequence finishes, an additional one-inch LED group 106 is deactivated to insure that small changes in strip 11 position do not cause false hole detect signals and to permit the strip 11 centerline to vary. The entire sequence may be completed in 10 milliseconds. The auto-shutter circuit 108 is described in more detail below.

Figure 9A:
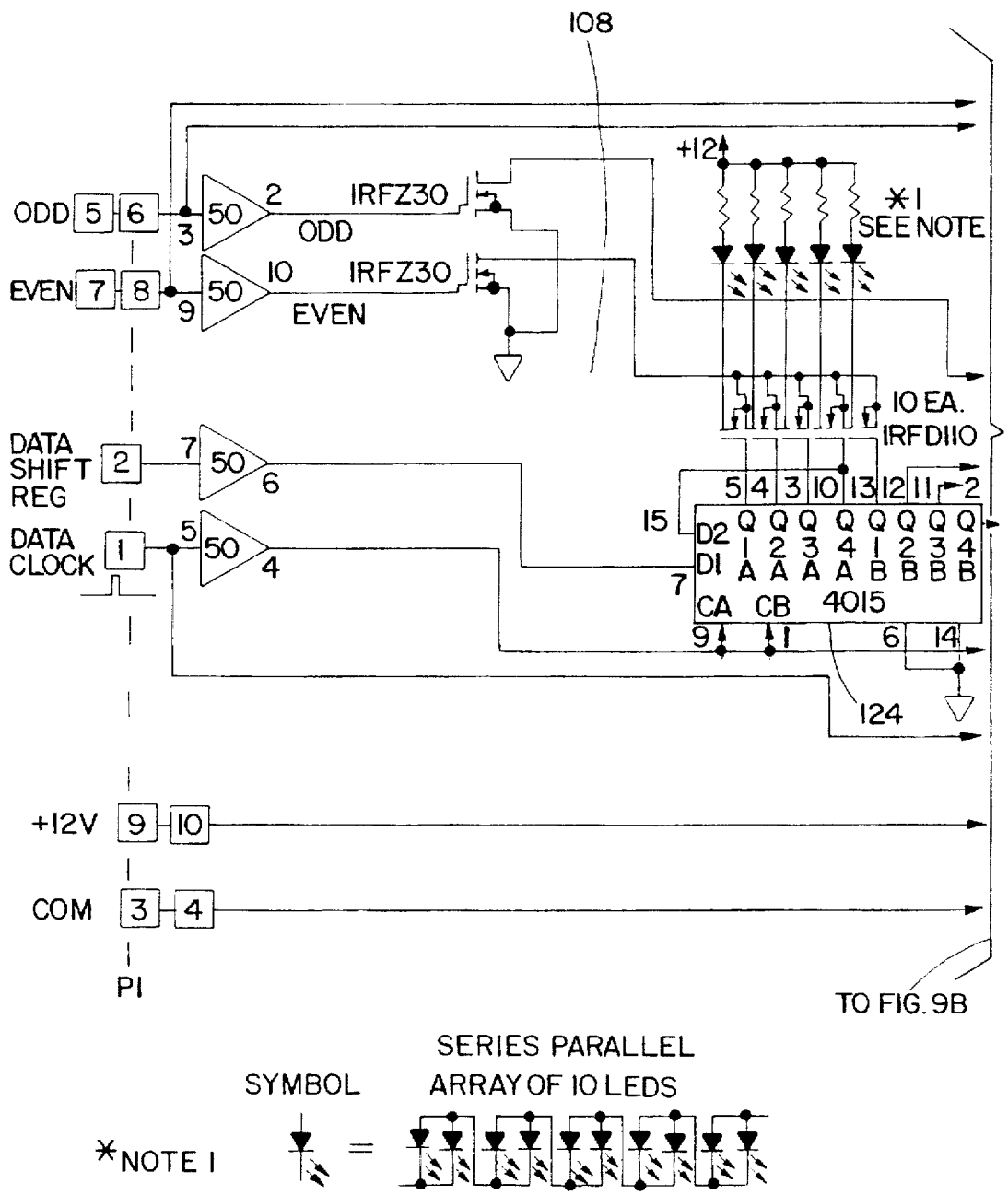
FIG. 9 is an example of an electrical schematic of the circuitry used to drive the LED array of the emitter.
Figure 9B:
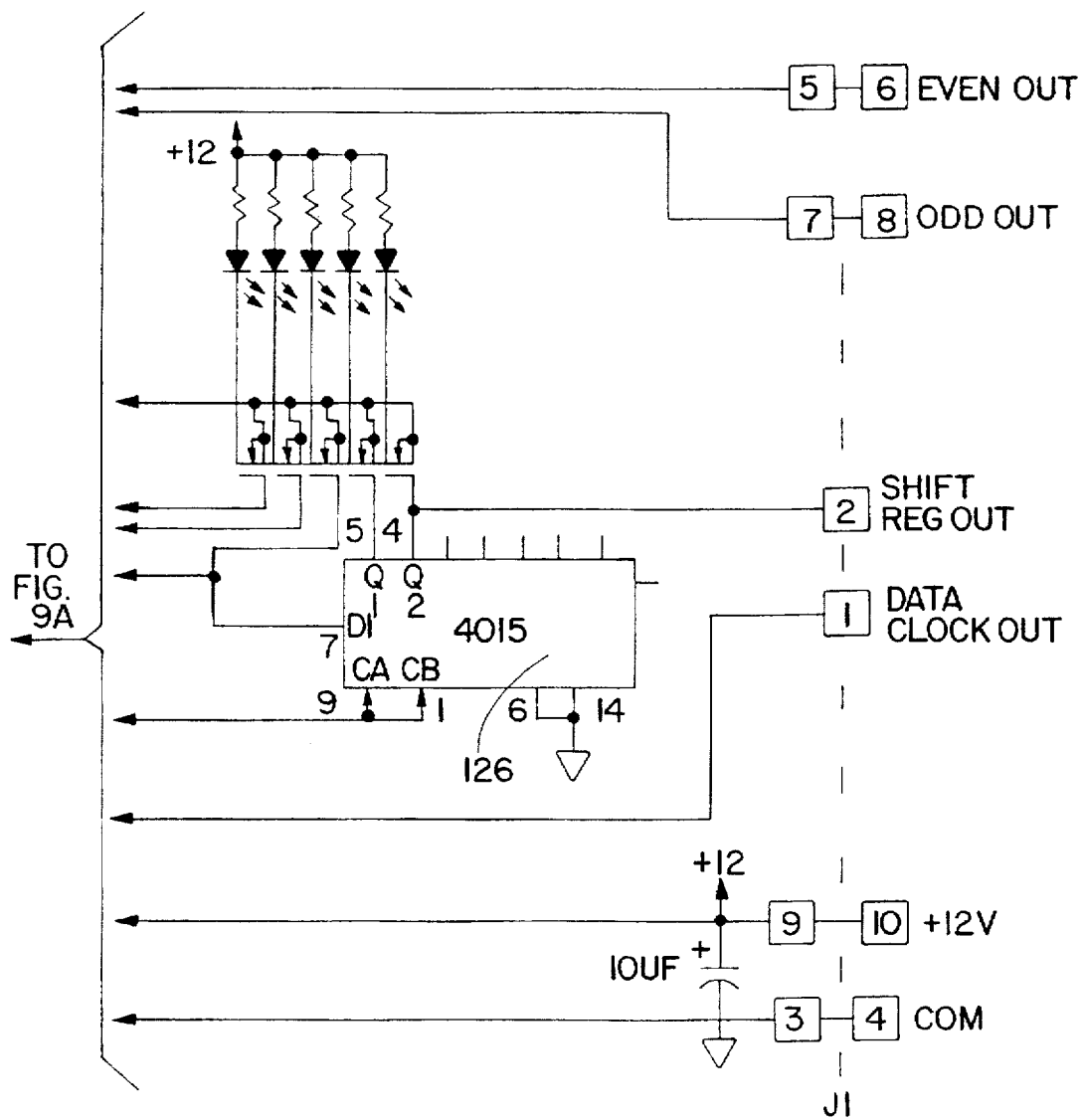

Referring again to FIG. 1, the strip 11 of material being scanned is placed between the emitter 12 and the receiver 14. As the strip 11 moves between the emitter 12 and the receiver 14, the array 18 of LEDs in the emitter 12 are pulsed, or scanned. FIG. 9 illustrates one example of the circuitry used to drive the LED array 18 of the emitter 12. If there is a hole in the strip 11, the light from the LEDs goes through the hole in the strip and is detected by the silicon photocells 20 in the receiver 14. The detector circuitry 40 in the receiver 14 sends a video signal to the video processing circuit 60 in the emitter 12. If the circuit in the emitter 12 determines that the video signal is not noise, the emitter 12 then sends a video signal (a 12 volt CMOS logic signal) to the processing unit 16 whenever a hole is detected. The processing unit 16 processes the video signal from the emitter 12 and activates the hole detect lamp 73.

Figure 7:
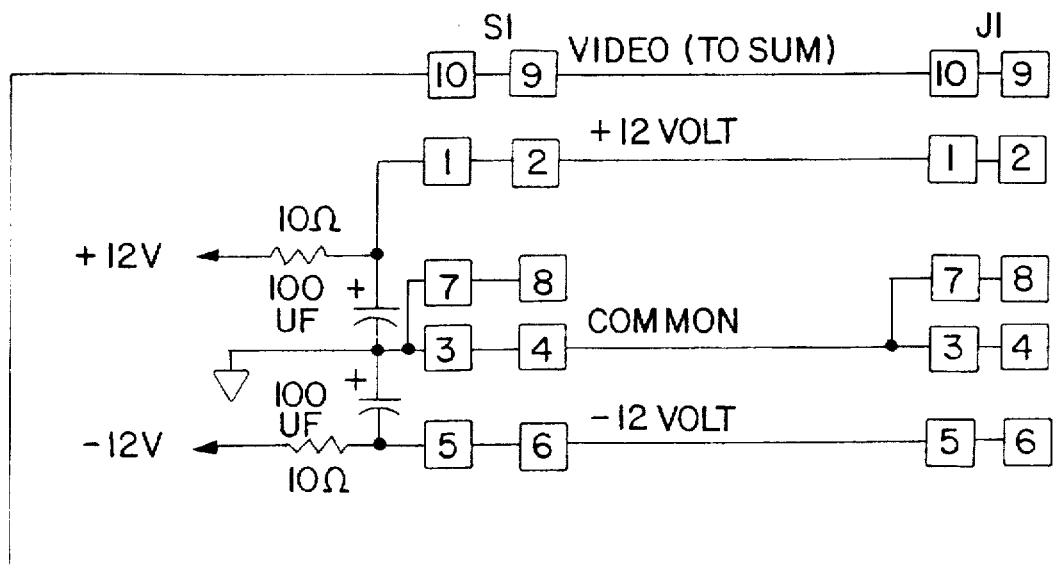
FIG. 7 is an example of the LED detect circuitry of the receiver of the present invention.
Figure 7:
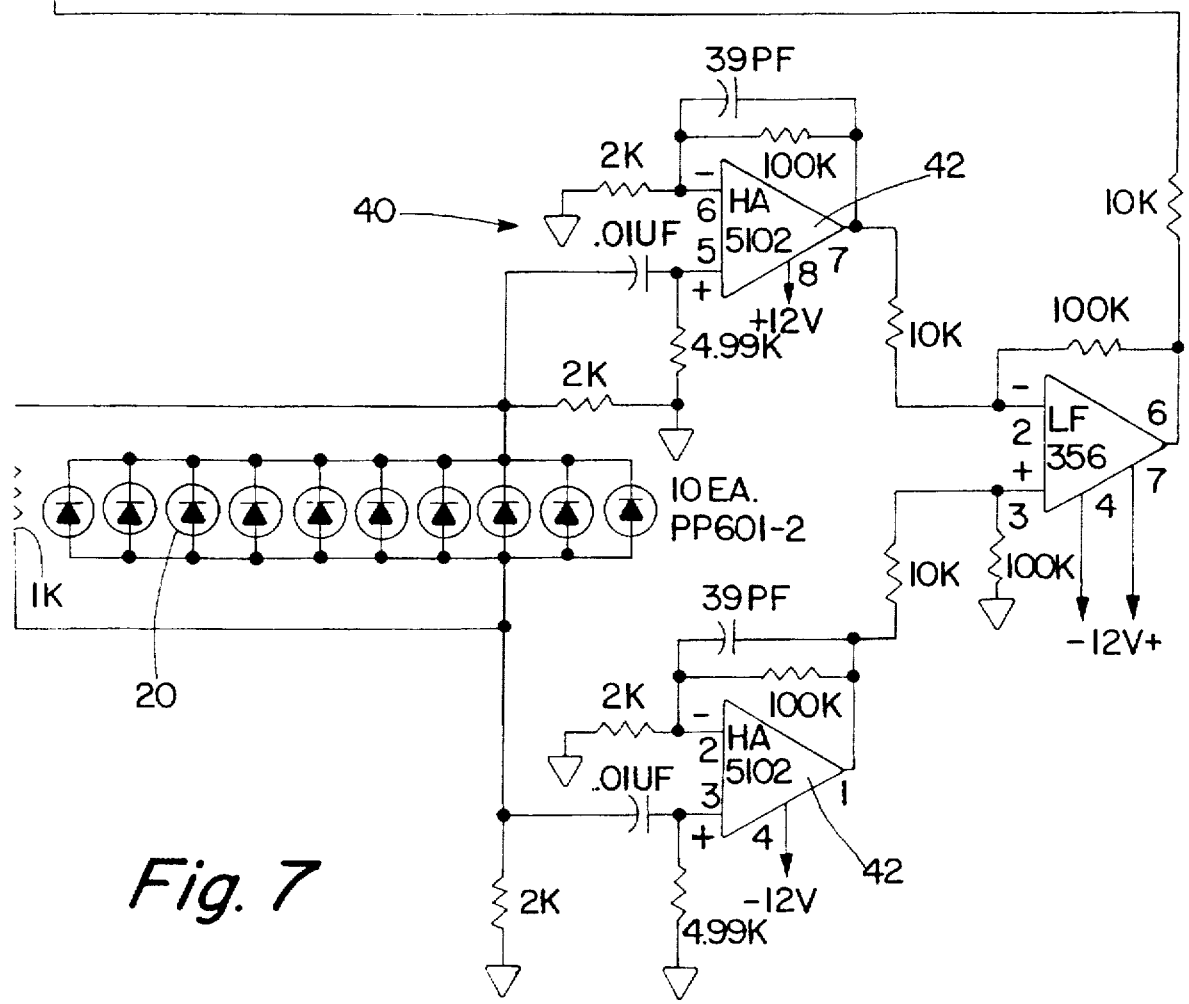
Figure 8:
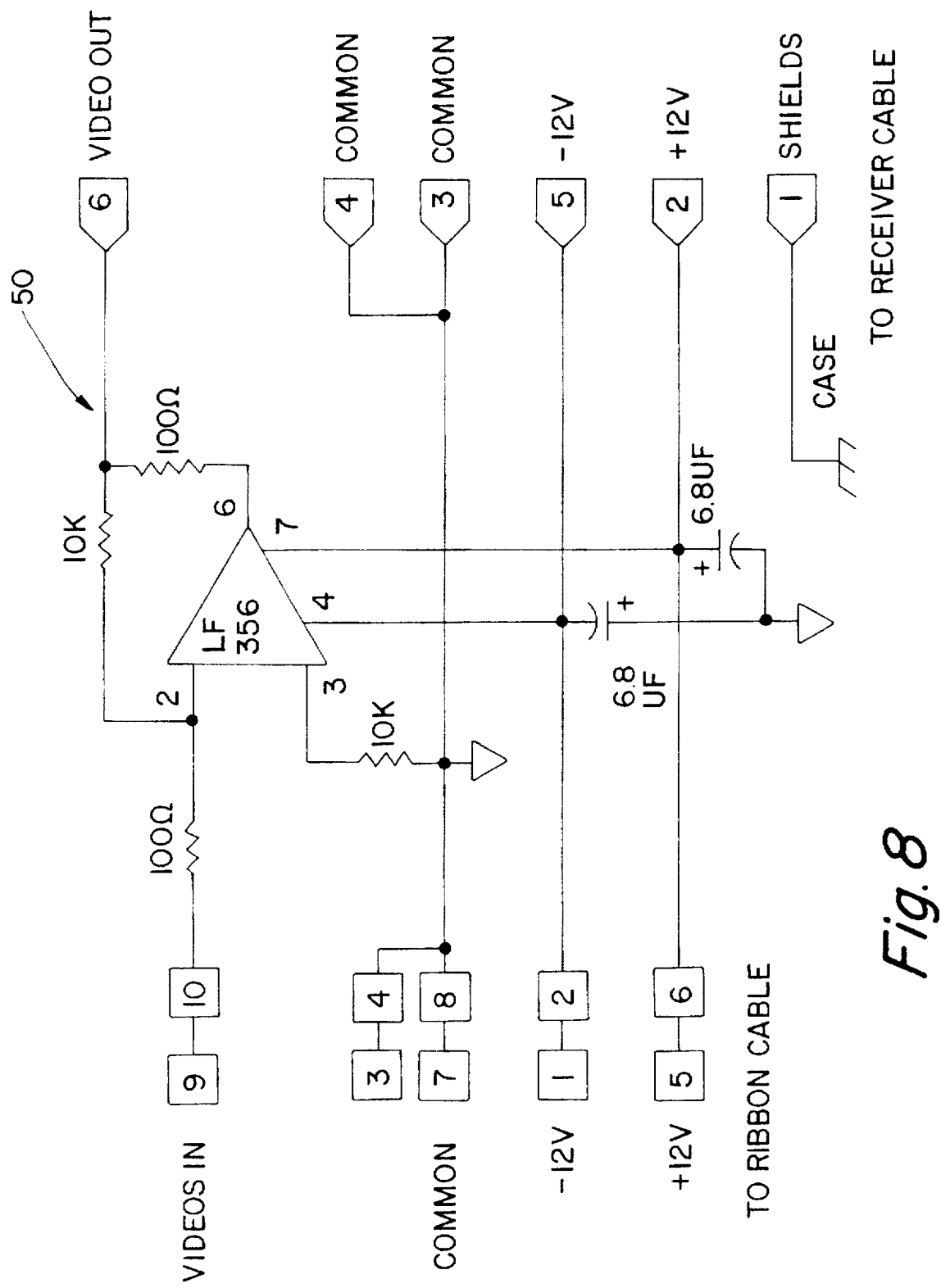
FIG. 8 is an example of an electrical schematic of the summing amplifier circuit of the present invention.

FIG. 7 illustrates one example of the LED detect circuitry 40 of a receiver 14. Each of the 10 silicon photocells 20 in the receiver 14 are fed into a pair of balanced amplifiers 42 (or "preamplifiers") designed to have a bandpass of 20 kHz. The voltage output of the LED detect circuitry 40 is then fed through a resistor to a summing amplifier circuit 50. FIG. 8 illustrates one example of the summing amplifier circuitry 50 of the present invention. The summing amplifier circuit 50 outputs a video signal which is then sent to the emitter 12 via the receiver-to-emitter cable 24 to be processed.

Figure 10A:
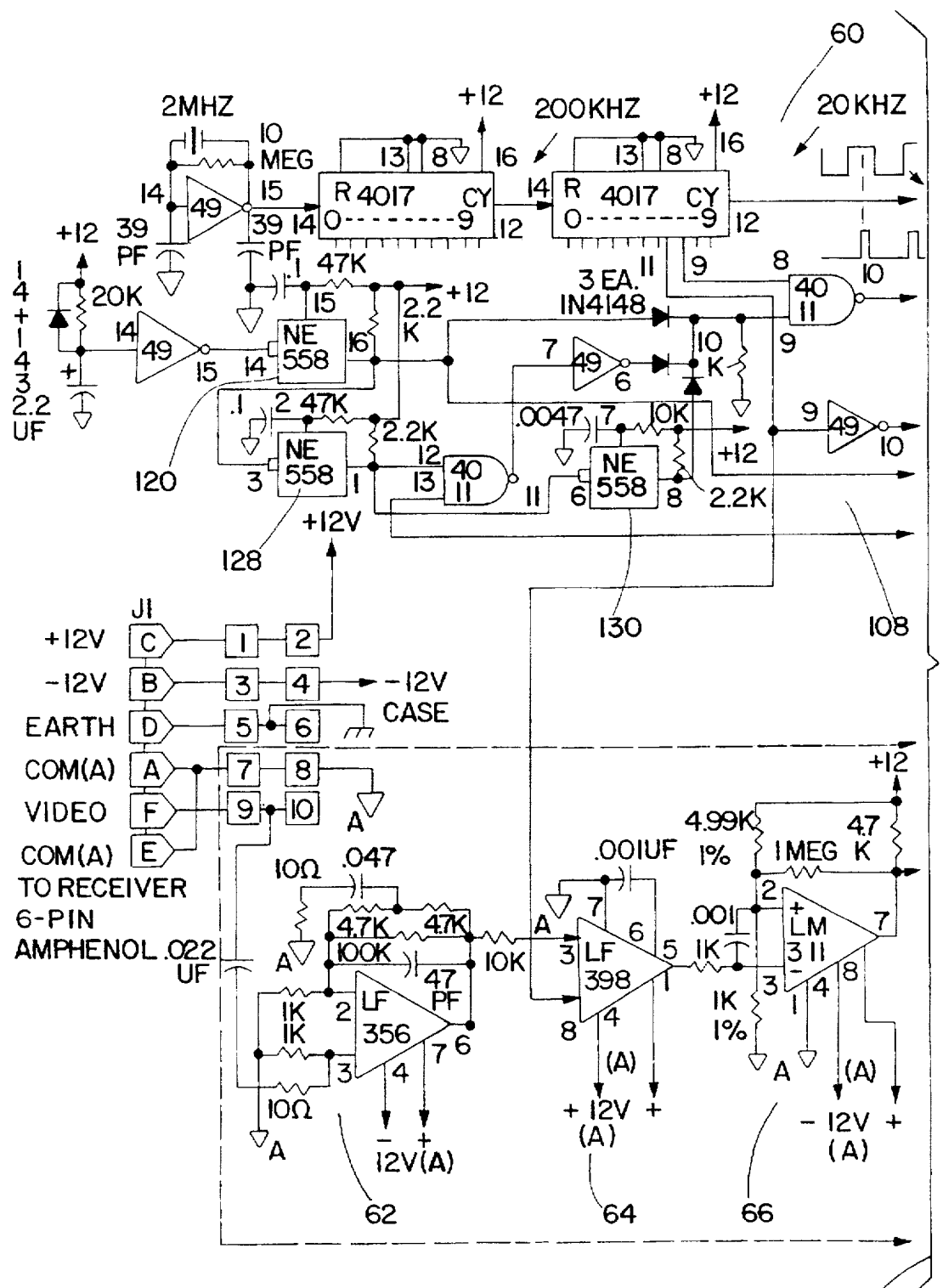
FIG. 10 is an example of an electrical schematic of the video signal processing circuit of the present invention.
Figure 10B:
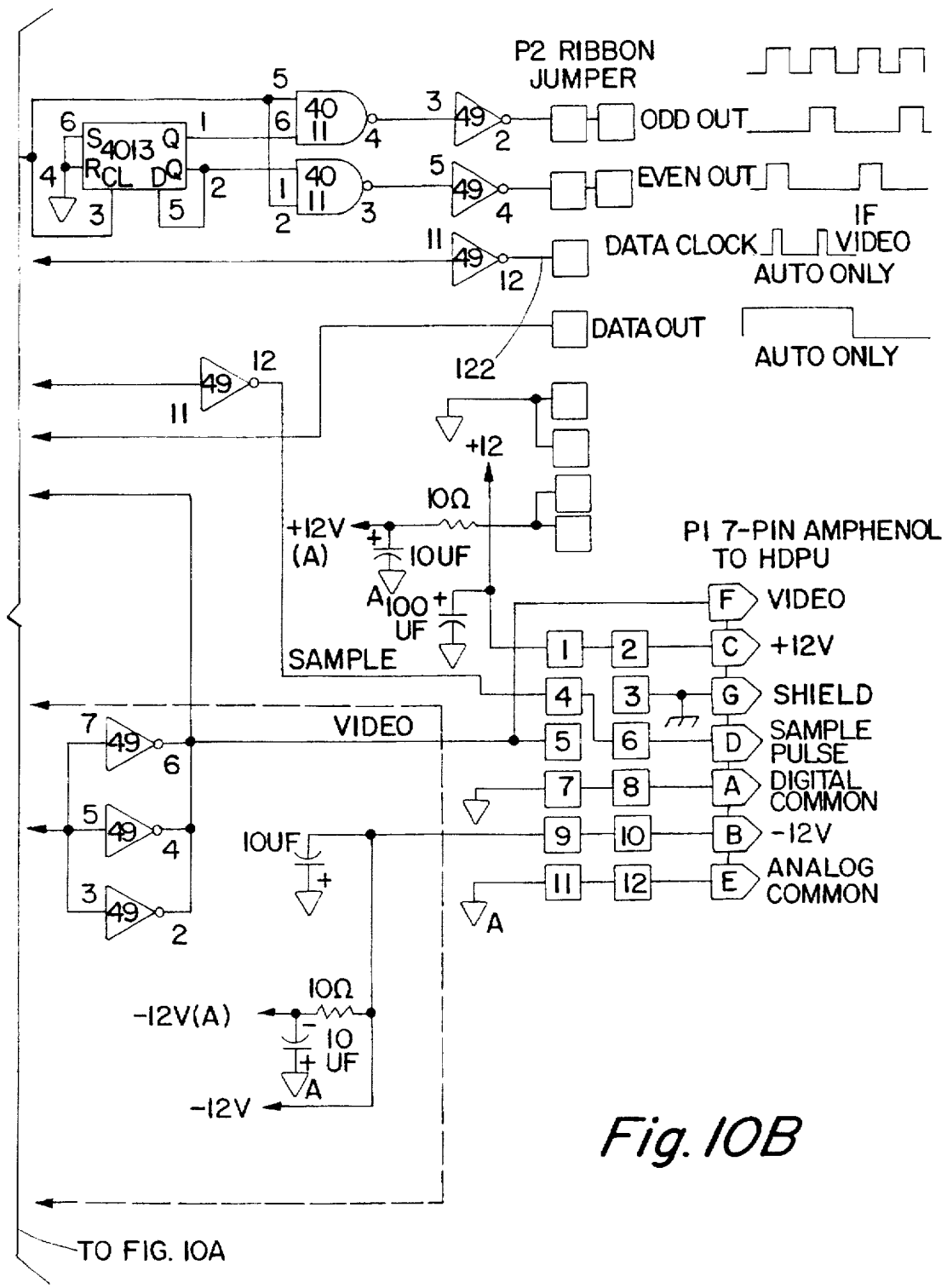

FIG. 10 illustrates one example of the video signal processing circuitry 60 of the emitter 12. The video signal from the receiver 14 is fed into a sharply tuned 20 kHz bandpass amplifier 62. The output of the bandpass amplifier 62 is then fed into a sample and hold amplifier 64 whose output is then fed to a comparator 66. If the video signal exceeds the trigger level (the light amplitude trigger level is 2 volts), the comparator 66 switches from 0 to 12 volts (indicating that the video signal is real and not merely noise). If the trigger level is not exceeded, the switching does not occur. This 12 VDC CMOS signal is then sent to the processing unit 16.

Figure 11:
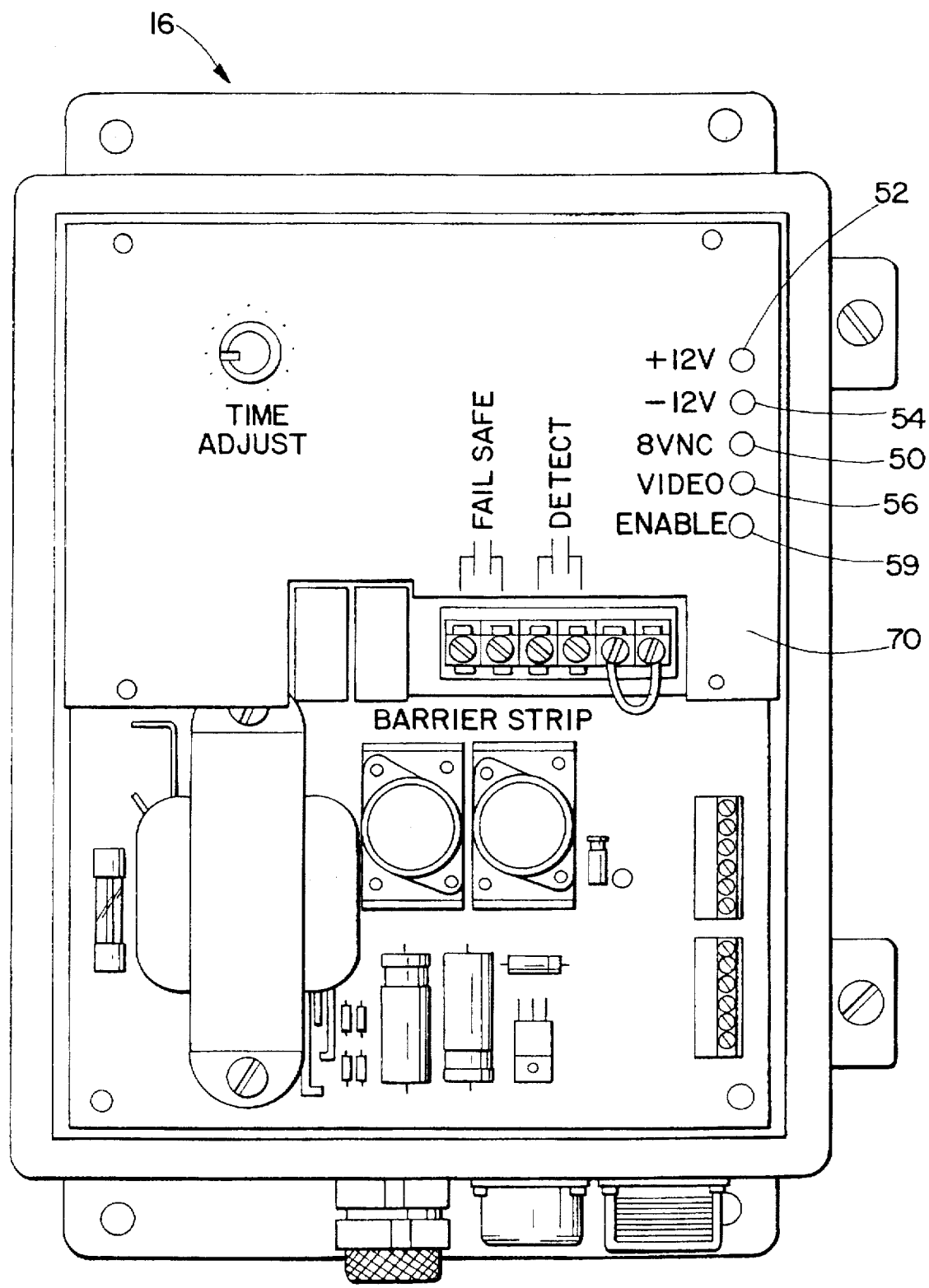
FIG. 11 illustrates an internal view of the processing unit of the present invention.

FIG. 11 illustrates the internal view of the processing unit 16. The processing unit 16 processes the signal from the emitter 12 in the "Hole Detection Personality Module" 70 located inside the processing unit 16. The processing unit 16 also processes a "SYNC" signal from the sensor 26. The SYNC signal is a 12 VDC CMOS logic (positive) pulse of 5 usec. The SYNC signal is a pulse signal generated by the end of the scan in an emitter 12 (the pulse length depends on the length of the emitter 12).

The diagnostic indicators are also placed within the processing unit 16. When the diagnostic indicators are functioning properly:

a) the +12 and −12 volt indicators 52, 54 should be fully lit when power is turned on to the unit.

b) the VIDEO indicator 56 will light more brightly as more of the emitter 12 light is detected by the receiver 14. When the emitter 12 is completely covered, the lamp should not light. If the VIDEO indicator 56 is still lit when the emitter 12 is completely covered, there may be a problem with ambient light interference.

c) the SYNC indicator 58 lights when a valid start of the scan sync pulse is being received from a working sensor 26.

d) the enable indicator 59 lights when the enable jumper is installed or an external switch is closed.

Figure 12A:
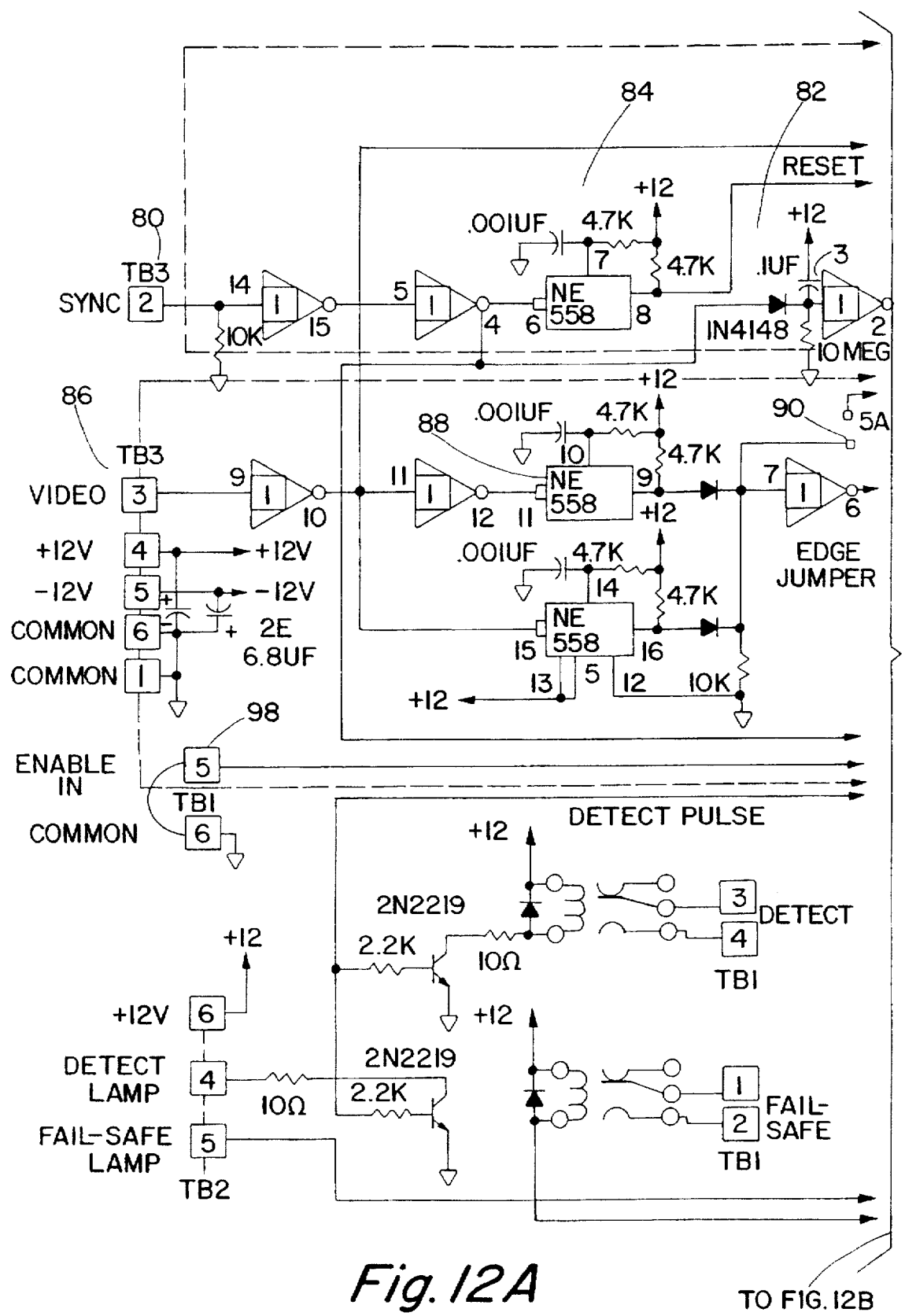
FIG. 12 is an example of an electrical schematic of the hole detect circuit and Fail-Safe circuit of the Hole Detection System of the present invention.
Figure 12B:
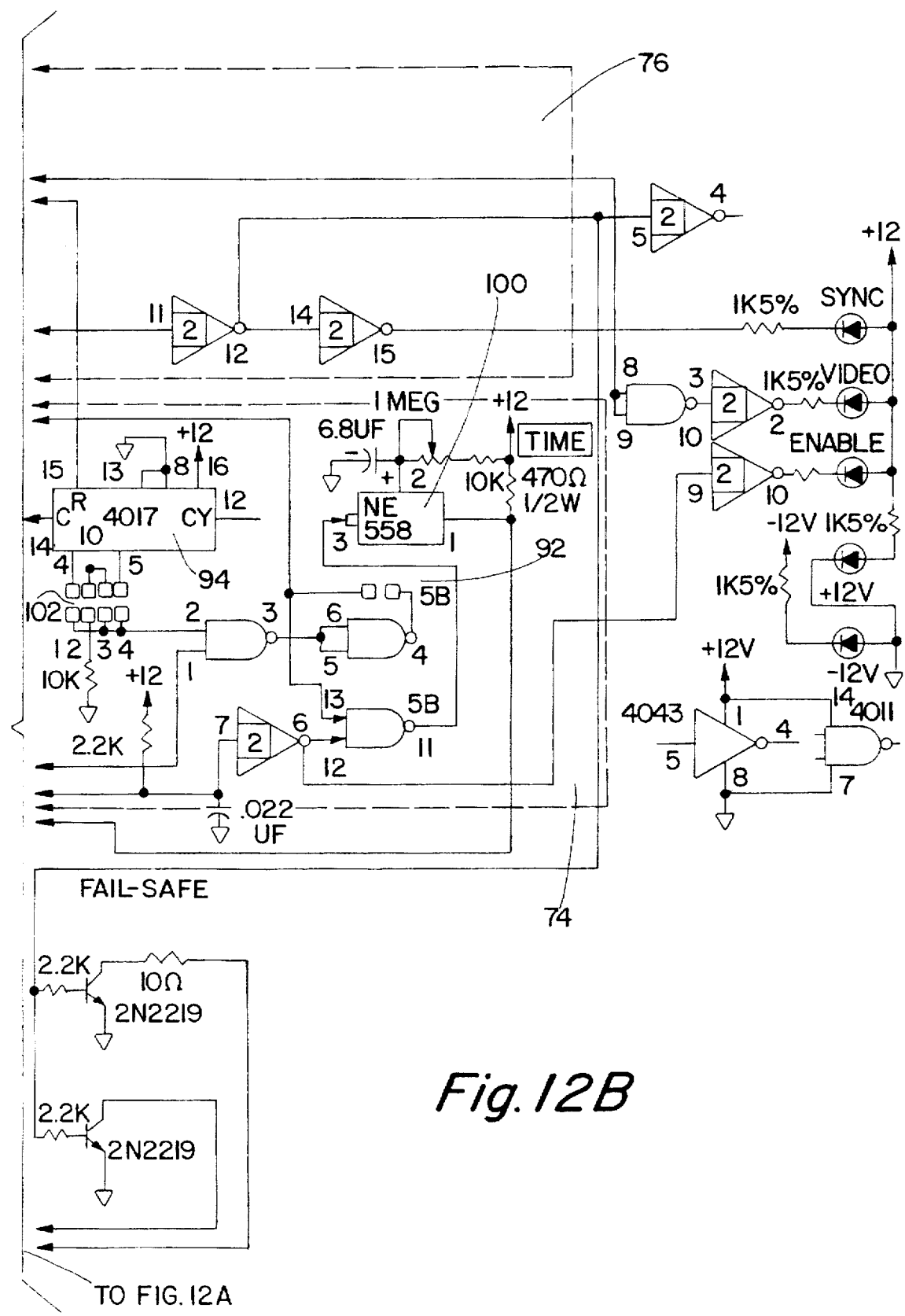

FIG. 12 illustrates one example of the hole detect circuit and the "Fail-Safe" circuit 76. The "Fail-Safe" circuit 76, located in the processing unit 16, monitors the SYNC signal input 80 from the sensor 26 to insure that the sensor 26 is scanning and that the power supply is operating properly.

The output from the Fail-Safe circuit 76 is connected to a Fail-Safe relay and also to a Fail-Safe indicator 72 mounted on the front panel of the processing unit 16. When scanning properly, the Fail-Safe relay contacts will close. The Fail-Safe circuitry 76 compares the 12 volts signal from the sensor 26 to a zener diode reference 82, and monitors the SYNC pulse and the sensors 26 to assure that the SYNC signal is regular and uninterrupted. If all these conditions are met, then the Fail-Safe lamp 72 is lighted and the Fail-Safe relay is closed.

The SYNC signal from the sensor 26 is used by the Personality Module circuit to clock each sensor scan into the hole detect circuit 74. In one embodiment of the hole detect circuit 74, a connection at jumper 5A 90 is made and the connection at jumper 5B 92 is left open (and thus jumpers 1–4 shown at 102 are bypassed). Thus this embodiment of the hole detect circuit 74 will trigger a hole detect signal for any pulse on the video input 86. The hole detect circuit 74 looks for any video pulse on a leading edge from the video input 86, and then fires a 1-shot NE558 at 88 indicating a hole has been detected. If the enable input 98 is enabled, this hole detect signal will fire the 1-shot NE558 at 100. This final hole detect signal will then activate the hole detect lamp 73 and close the detect relay contact.

FIG. 9 and FIG. 10 contain one example of the auto-shutter circuit of the present invention, shown generally at 108. The portion of the auto-shutter circuit 108 in FIG. 10 is the trigger circuit. The trigger circuit creates the control signals necessary to perform the auto-shutter process. Upon power up, the NE558 at 120 generates a signal which enables the data clock output 122 for the purpose of setting the shift register 124, 126 outputs to the "on" position. Turning the shift register 124, 126 outputs to the "on" position turns on all the LEDs of the array 18. If a video signal is recognized (again by the video signal processing circuitry 60 of the emitter 12), a NE558 at 128 fires which acts to turn off the video pulses As the auto-shutter sequence finishes, an additional one-inch LED group 106 is deactivated, by the NE558 at 130, to insure that small changes in strip 11 position do not cause false hole detect signals.

The emitter 12 and receiver 14 are highly resistant to most of the industrial environments that can cause problems with edge sensing equipment. The preferred operating temperature for the sensor 26 is 32° F. to 122° F. Operations outside this range are possible with special provisions made to protect the equipment, such as heat shields and water jackets. In cases of high degrees of foreign material interfering with the sensor 26 scans, a simple air wipe installed over the emitter 12 window can be helpful where contamination cannot be avoided.

Since the sensor 26 is producing and looking for light modulated at approximately 20 kHz, it is unlikely that most ambient light sources will be a problem. However, when special conditions require, filters may be provided to reduce the problem of ambient light.

In applications where the sensor 26 may be vulnerable to strip collisions, the enclosures of the emitter 12 and receiver 14 can be designed to withstand most industrial conditions, including high moisture environments and corrosive conditions.

What is claimed is:

1. A system for detecting small holes in moving sheet products, comprising:

an array of LEDs;

an array of photocells positioned directly across from said array of LEDs for detecting light emitted from said array of LEDs;

a preamplifier circuit electrically connected to said photocells;

a video processing circuit electrically connected to said preamplifier circuit for processing a video signal from said preamplifier circuit and wherein said video processing circuit outputs an appropriate video signal when a hole is detected in said moving sheet product;

a processing unit electrically connected to said video processing circuit for processing a video signal from said video processing circuit, and wherein said processing unit indicates when a hole in said moving sheet material has been detected.

2. A hole detection system as recited in claim 1 wherein said video processing circuit is comprised of:

a sharply tuned bandpass filter electrically connected to said preamplifier circuit for filtering said video signal from said preamplifier circuit, wherein said sharply tuned bandpass filter has an output;

a sample and hold amplifier electrically connected to said output of said preamplifier circuit, wherein said sample and hold amplifier has an output;

a comparator electrically connected to said output of said sample and hold amplifier for filtering noise; and wherein said comparator switches to a higher voltage when said video signal from said preamplifier circuit exceeds the threshold voltage of said comparator.

3. A hole detection system as recited in claim 1 wherein said array of photocells is comprised of infrared sensitive silicon cells, and wherein said photocells are evenly distributed along said array.

4. A hole detection system as recited in claim 1 further comprising:

a cylindrical lens over said array of photocells for concentrating the field of view for said array of photocells;

wherein said cylindrical lens allows closer spacing of said array of LEDs and said array of photocells to accommodate limited space requirements and to improve the signal to noise ratio of said hole detection system.

5. A hole detect system as recited in claim 1, further comprising:

a filter placed over said array of photocells for reducing ambient light and for removing the infrared spectrum energy.

6. A hole detection system as recited in claim 1; wherein said processing unit is comprised of:

a hole detect circuit electrically connected to said video processing circuit for triggering a hole detect signal when a hole is detected on said moving sheet material; and a "Fail-Safe" circuit electrically connected to said hole detect circuit for insuring that said hole detection system is scanning properly.

7. A hole detect system as recited in claim 6, wherein said processing unit is further comprised of:

a edge counting circuit electrically connected to said hole detect circuit for counting edges detected in a scan.

8. A hole detection system as recited in claim 1, wherein said array of LEDs is comprised of:

a first section of 50 LEDs;

a second section of 50 LEDS;

wherein said first section of 50 LEDs is comprised of five groups of 10 LEDS; and wherein said second section of 50 LEDs is comprised of five groups of 10 LEDs.

9. The hole detection system of claim 8, wherein said first and second sections of LEDs are pulsed at a 20 kHz repetition rate.

10. A hole detect system as recited in claim 8, further comprising:
an auto-shutter circuit electrically connected to said array of LEDs.

11. A method of detecting small holes in moving sheet materials, comprising the steps of:
(a) positioning an array of electromagnetic radiation emitting devices a distance from a surface of material being scanned;
(b) positioning a receiver a stand-off distance from an opposite side of said material being scanned, said receiver responsive to said electromagnetic radiation emitted from said emitting devices;
(c) energizing said array of electromagnetic radiation emitting devices;
(d) providing a signal when said receiver detects radiation emitted from said emitting devices;
(e) processing said signal to obtain small hole detection information; and
(f) automatically adjusting said array of emitting devices for different strip widths being scanned, wherein said automatic adjusting of said emitting devices includes:
energizing the emitting devices in said array; and
deactivating a group of emitting devices of said array of emitting devices if light is detected in said receiver.

12. The method of claim 11, wherein said array of emitting devices is sequentially energized.

13. The method of claim 12, wherein said array of emitting devices is sequentially energized at a 20 kHz rate.

14. The method of claim 11, further comprising the step of:
deactivating an additional group of said array of emitting devices to insure that small changes in material position does not cause false hole detection signals.

15. The method of claim 11, further comprising the step of:
activating a hole detect indicator when said signals received from said receiver indicate a hole has been detected in said material being scanned.

16. The method of claim 11, further comprising the step of:
placing a cylindrical lens over said receiver for concentrating the field of view of said receiver;
wherein said cylindrical lens allows closer spacing of said array of LEDs and said array of photocells to accommodate limited space requirements and to improve the signal to noise ratio of said hole detection system.

17. The method of claim 11, further comprising the steps of:
counting edges detected in a scan; and
indicating a hole has been detected only when a proper number of edges has been counted during the last scan.

18. The method of claim 11, further comprising:
spacing said array of electromagnetic radiation emitting devices and said electromagnetic radiation receiver closer that two times the length of said array of emitting devices, wherein said spacing improves small hole sensitivity.

19. The method of claim 11, further comprising:
providing a SYNC signal after energizing said array of electromagnetic radiation emitting devices;
monitoring said SYNC signal to insure said SYNC signal is regular and uninterrupted; and
activating a Fail-Safe indicator lamp when said SYNC signal is regular and uninterrupted.

20. A system for detecting small holes in moving sheet products, comprising:
an array of LEDs;
an array of photocells positioned directly across from said array of LEDs for detecting light emitted from said array of LEDs and wherein said array of photocells is comprised of infrared sensitive silicon cells, and wherein said cells are evenly distributed along said array;
a preamplifier circuit electrically connected to said photocells;
a video processing circuit electrically connected to said preamplifier circuit for processing a video signal from said preamplifier circuit, wherein said video processing circuit outputs an appropriate video signal when a hole is detected in said moving sheet product, and wherein said video processing unit includes a:
bandpass filter electrically connected to said preamplifier circuit for filtering said video signal from said preamplifier circuit, a sample and hold amplifier electrically connected to an output of said preamplifier circuit, and a comparator electrically connected to an output of said sample and hold amplifier for filtering noise;
a processing unit electrically connected to said video processing circuit for processing a video signal from said video processing circuit, wherein said processing unit indicates when a hole in said moving sheet material has been detected, and wherein said processing unit includes:
a hole detect circuit electrically connected to said video processing circuit for triggering a hole detect signal when a hole is detected on said moving sheet material, a "Fail-Safe" circuit electrically connected to said hole detect circuit for insuring said hole detection system is scanning properly, and an edge counting circuit electrically connected to said hole detect circuit for counting edges detected in a scan.

* * * * *